United States Patent
Raanan et al.

(10) Patent No.: US 10,561,344 B2
(45) Date of Patent: Feb. 18, 2020

(54) FALL DETECTION DEVICE AND METHOD

(71) Applicant: Hip Hope Technologies Ltd., Hod HaSharon (IL)

(72) Inventors: Amatsia Raanan, Raanana (IL); Ran Manor, Toronto (CA)

(73) Assignee: Hip Hope Technologies Ltd., Hod-HaSharon (IL)

( * ) Notice: Subject to any disclaimer, the term of this patent is extended or adjusted under 35 U.S.C. 154(b) by 419 days.

(21) Appl. No.: 15/511,247

(22) PCT Filed: Sep. 16, 2015

(86) PCT No.: PCT/IB2015/057129
§ 371 (c)(1),
(2) Date: Mar. 15, 2017

(87) PCT Pub. No.: WO2016/042498
PCT Pub. Date: Mar. 24, 2016

(65) Prior Publication Data
US 2017/0281056 A1  Oct. 5, 2017

Related U.S. Application Data

(60) Provisional application No. 62/050,777, filed on Sep. 16, 2014.

(51) Int. Cl.
*A61B 5/00* (2006.01)
*A61B 5/11* (2006.01)

(52) U.S. Cl.
CPC .......... *A61B 5/1117* (2013.01); *A61B 5/6823* (2013.01); *A61B 5/6831* (2013.01); *A61B 5/7282* (2013.01); *A61B 2562/0219* (2013.01)

(58) Field of Classification Search
CPC ....... A61B 5/11; A61B 5/1116; A61B 5/1117; A61B 5/1121; A61B 5/1122; A61B 5/6823; A61B 5/6831; A61B 5/7282
See application file for complete search history.

(56) References Cited

U.S. PATENT DOCUMENTS 8,805,641 B2 *   8/2014   Greene ................ A61B 5/1038
                                                          702/145
8,909,497 B1 *  12/2014   Shkolnikov ............. G01P 15/00
                                                          340/573.1

(Continued)

*Primary Examiner* — Max F Hindenburg
(74) *Attorney, Agent, or Firm* — Dr. Hanan Farber Patent Agent Ltd.

(57) ABSTRACT

Detection of a fall of a user wearing the device. A processor is configured to time sample and to input multiple values over time of: the acceleration vector, the angular velocity and the point-to-point distance. The processor is configured to determine over time the direction of gravity from the acceleration vector. The processor is configured to integrate over time the angular velocity to produce an orientation angle of the protection device relative to the direction of gravity. The processor, responsive to the point-to-point distance and the orientational angle, is configured to determine heights over time of the distance sensor from the ground. The processor is configured to indicate initiation of a potential fall event by a change in downward acceleration measured by the accelerometer or a rapid decrease in the determined heights of the distance sensor from the ground. The processor is configured, responsive to the point-to-point distance and the orientation angle, to determine at least one height before the initiation of the potential fall event and at least one height after the initiation of the potential fall event of the distance sensor from the ground.

20 Claims, 6 Drawing Sheets

(56) References Cited

U.S. PATENT DOCUMENTS

| | | | | |
|---|---|---|---|---|
| 9,179,864 B2* | 11/2015 | Otto | .................... | A61B 5/1118 |
| 9,412,252 B2* | 8/2016 | Yi | .................... | G08B 21/0446 |
| 2009/0254003 A1* | 10/2009 | Buckman | ............. | A61B 5/1117 |
| | | | | 600/595 |
| 2012/0101411 A1* | 4/2012 | Hausdorff | ............. | A61B 5/1117 |
| | | | | 600/595 |
| 2013/0312168 A1* | 11/2013 | Raanan | ............. | A41D 13/0506 |
| | | | | 2/465 |
| 2014/0123374 A1* | 5/2014 | Gelston | ............... | A41D 13/018 |
| | | | | 2/455 |
| 2014/0148733 A1* | 5/2014 | Stone | .................... | A61B 5/004 |
| | | | | 600/595 |
| 2014/0247335 A1* | 9/2014 | Hanson | ............... | A61B 5/0077 |
| | | | | 348/77 |
| 2014/0276238 A1* | 9/2014 | Osorio | ................. | A61B 5/0205 |
| | | | | 600/595 |
| 2015/0164377 A1* | 6/2015 | Nathan | ................ | A61B 5/1122 |
| | | | | 600/595 |
| 2016/0203692 A1* | 7/2016 | Ten Kate | ............. | G08B 21/043 |
| | | | | 340/573.1 |

* cited by examiner

FALL DETECTION DEVICE AND METHOD

BACKGROUND

1. Technical Field

The present invention relates to a wearable device for performing fall detection.

2. Description of Related Art

Each year, millions of elderly people around the world especially women experience falls resulting in hip fractures mainly, femoral neck fractures. Hip fractures in the elderly result in physical suffering, loss of independence, a deteriorating mental state and high mortality rate.

US patent application publication, US20130312168 of the present Applicant, discloses an active hip protector system and method for hip fracture prevention including a belt-like pouch, worn over the user's waist, containing airbags which are inflated to a large size ensuring that the user's thighs will not hit the ground upon impact, once the system detects a fall. The pouch contains distance measurement sensors, acceleration and spatial orientation sensors. A pneumatic system, including the airbags, is carried within the pouch or in another location.

BRIEF SUMMARY

Various devices and methods are disclosed herein for detection of a fall of a user wearing the device. The device includes a processor, an acceleration sensor operatively attached to the processor. The acceleration sensor is configured to sense an acceleration vector of the protection device. A gyroscope sensor is operatively attached to the processor. The gyroscope sensor is configured to sense an angular velocity of the device. A distance sensor is operatively attached to the processor. The distance sensor is oriented to measure a point-to-point distance between the protection device and a point on the ground. The processor is configured to time sample and to input multiple values over time of: the acceleration vector, the angular velocity and the point-to-point distance. The processor is configured to determine over time the direction of gravity from the acceleration vector. The processor is configured to integrate over time the angular velocity to produce an orientation angle of the protection device relative to the direction of gravity. The processor, responsive to the point-to-point distance and the orientational angle, is configured to determine heights over time of the distance sensor from the ground. The processor is configured to indicate initiation of a potential fall event by a change in downward acceleration measured by the accelerometer or a rapid decrease in the determined heights of the distance sensor from the ground. The processor is configured, responsive to the point-to-point distance and the orientation angle, to determine at least one height before the initiation of the potential fall event and at least one height after the initiation of the potential fall event of the distance sensor from the ground.

The processor may be configured to determine from a downward acceleration determined from the accelerometer, a height (of the accelerometer from the ground) less than a predetermined threshold height at a time $t_f$ indicating an imminent fall, and to determine the at least one height of the distance sensor after the initiation of the potential fall event during a predetermined time interval before the time $t_f$.

The processor may be configured to verify an expectation of completion of a fall by correlating the at least one height after the initiation the potential fall event with a computed height predicted from a simultaneous measured acceleration component in the downward direction.

The processor may be configured to verify an expectation of completion of a fall by correlating a velocity determined from the at least one height before the potential fall event and the at least one height after the potential fall event with a velocity predicted by integrating a simultaneous measured acceleration component in the downward direction.

The processor is configured to verify an expectation of completion of a fall by correlating a downward acceleration determined from the at least one height before the potential fall event and the at least one height after the potential fall event with a simultaneous measured acceleration component in the downward direction.

A protection device, e.g. air bag, may be connectable to the processor. The protection device responsive to an activation by the processor is configured to protect the user from the fall.

The processor may be configured to activate the protection device when the computed heights rapidly decrease over time except: (i) when the decrease of the computed heights is followed by an increase in computed heights indicating that the user is exercising or (ii) when theat least one height before a fall and the at least one height after a fall are substantially uncorrelated with a computed height predicted from simultaneous measured acceleration in the downward direction as measured by the accelerometer characteristic of the user standing on a means of transportation.

The processor is configured to activate the protection device when the heights rapidly decrease corresponding to falling except: (iii) when the heights computed are discontinuous over time indicating that the variations in heights are characteristic of being computed from a ground surface to being computed from an object on the ground surface or (iv) when the decrease of height computations is characteristic of the user ascending or descending a stairway.

The acceleration vector as sensed by the acceleration sensor may include a constant acceleration of gravity and may include a dynamic acceleration due to movement of the user. The downward direction of gravity may be determined by: (i) determining that the user wearing the detection device is not moving and the downward direction is determined by the constant acceleration of gravity and/or (ii) averaging the acceleration vectors over a time period while the user wearing the detection device is moving and determining the downward direction of gravity from the resultant average.

Actuation of the protection device may be prevented when the acceleration sensor indicates downward acceleration characteristic for example of elevator usage yet unaccompanied by a rapid decrease in the heights of the distance sensor above the ground surface.

Under control of a micro-controller, heights of the device above floor or ground are respectively computed over time. Initiation of a potential fall event is indicated by a rapid decrease in heights and/or by a discontinuous acceleration. Initiation of a potential fall event is verified as a real fall event by at least one height computation after the potential fall event of the device from the floor or to the ground. A protection device may be actuated if the computed height(s) after the potential fall event is/are also indicative of a real fall event.

Upon indicating the potential fall event, the sampling measurement rates used for height computations may be increased and the height computations after the potential fall event may be performed at a higher sampling rate.

Actuation of a protection device may be prevented when the height computation(s) after the potential fall event do/does not continue to decrease indicating a motion pattern such as exercising.

Actuation of a protection device may be prevented when the the height computation(s) after the potential fall event does/do not continue to decrease indicating that the user is standing on a moving means of transportation such as a bus or train.

Actuation of a protection device may be prevented when the the height computation(s) after the potential fall event does/dos not continue to decrease indicating that the height computations vary from being computed from a ground surface to being computed from an object placed on the ground surface.

Actuation of a protection device may be prevented when the the height computation(s) after the potential fall event is/are characteristic of the user descending or ascending a stairway.

Actuation of a protection device may be prevented when the acceleration sensor indicates a discontinuous change in acceleration characteristic of elevator usage and unaccompanied by a rapid decrease in the computed heights of the device from the elevator floor.

The foregoing and/or other aspects will become apparent from the following detailed description when considered in conjunction with the accompanying drawing figures.

BRIEF DESCRIPTION OF THE DRAWINGS

The invention is herein described, by way of example only, with reference to the accompanying drawings, wherein.

Figure 1:
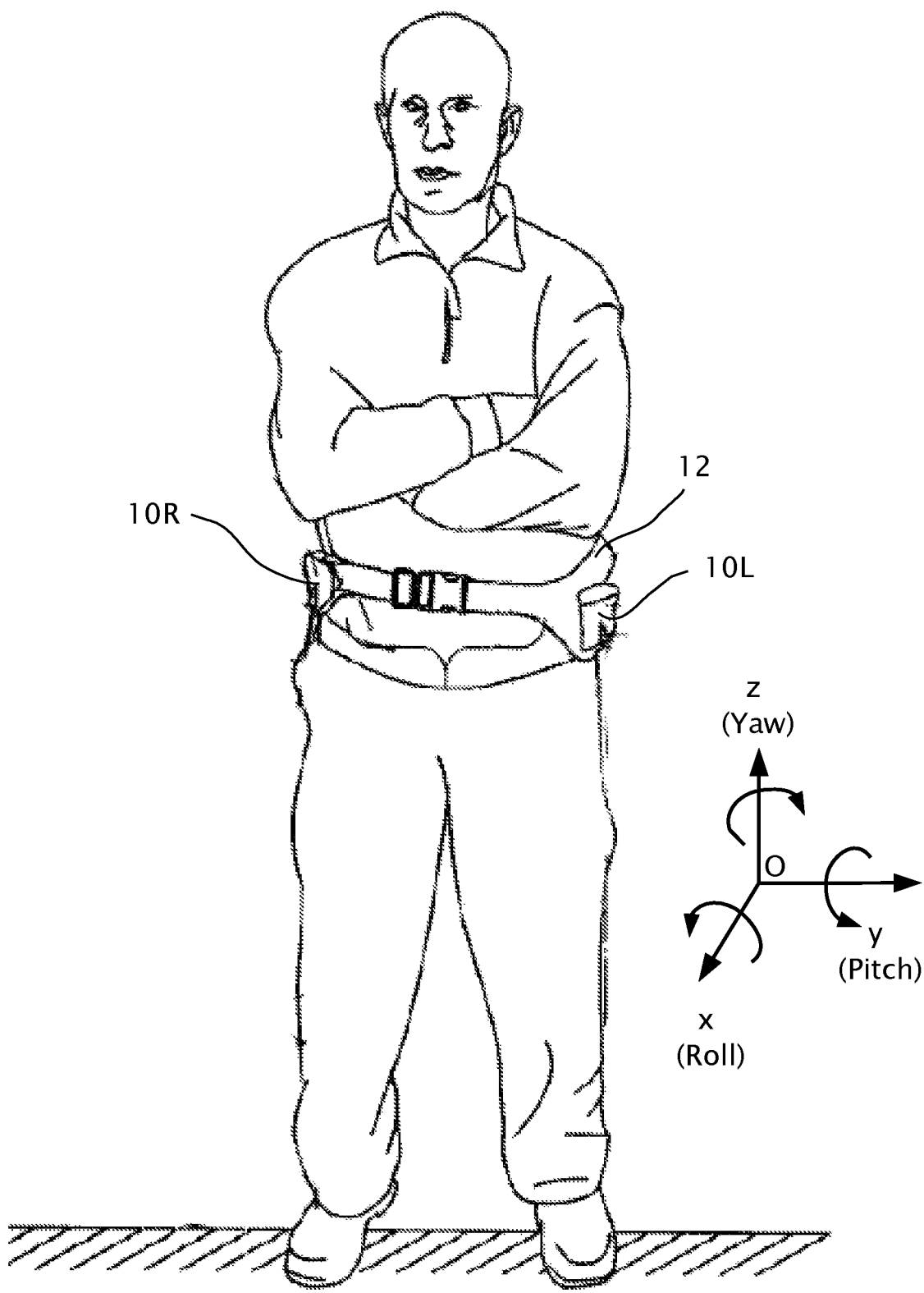
FIG. 1 illustrates an embodiment of a detection device worn by a person, according to feature of the present invention.

The foregoing and/or other aspects will become apparent from the following detailed description when considered in conjunction with the accompanying drawing figures.

DETAILED DESCRIPTION

Reference will now be made in detail to features of the present invention, examples of which are illustrated in the accompanying drawings, wherein like reference numerals refer to like elements throughout. The features are described below to explain the present invention by referring to the figures.

Before explaining features of the invention in detail, it is to be understood that the invention is not limited in its application to the details of design and the arrangement of the components set forth in the following description or illustrated in the drawings. The invention is capable of other features or of being practised or carried out in various ways and embodiments. Also, it is to be understood that the phraseology and terminology employed herein is for the purpose of description and should not be regarded as limiting.

By way of introduction, aspects of the present invention are directed to a fall detection device wearable for instance on the waist of a user, which is intended to reliably distinguish between actual falling and other events which may appear to be falling. In order to reliably distinguish between true falls and other events, height verification may be used throughout the fall process. Verification of the height calculated based on acceleration sensor(s) measurements is performed by a distance sensor which measures distance to a point on the ground or floor combined with an inclination or orientation angle measured by the gyroscope sensor.

To date, prior disclosures of active devices attempting to detect and protect a user against falls do not have sufficiently good results in reliably identifying falls with low false positive detection rates and unnecessary activation of protective means may result. In a practical and feasible active fall protection system false positive detections are maintained at nearly zero (for instance, no more than one false positive detection every several months). However, a decision to activate the protection element, e.g. air bag, must happen soon enough after the first indication that initiation of a potential fall event may be occurring in order to achieve protection by inflation of the protective element(s) before impact of the user with the floor. Additional distance sensing and height determination throughout at least the first part of the fall may be used to prevent false positive fall detection events without significantly lowering the true fall detection rates. Several events may appear as similar to actual falls and activation of the protection element(s) during these events may be prevented to achieve low false positive detection rates. These events include but are not limited to:

Elevator usage
Bus travel (while standing)
Going down stairs (fast pace is problematic)
Exercise In order to detect true falls and eliminate false positive activations after these and other similar events, three data points of height may be used. Two points may show a significant height decrease and provide an initiation of a potential fall event and one or additional points are used to verify after the initiation of the potential fall event that a real fall is occurring. The more height data points used prior to activation the better is the reliability of determination of a true fall event and elimination of false positive events. A change in measured acceleration $A_z$ in the downward (−Z) direction by an accelerometer may indicate initiation of a potential fall event. Verification of initiation of the potential fall event with a real expectation of a completion of a fall may be performed by measuring distance to the floor or ground. The distance measurement may be correlated with the measurement of acceleration in the downward direction. The correlation may be performed in several ways, differentiation of the distance measurement and/or by integration of the downward acceleration measurement.

Elevator usage may appear to be falling due to the abrupt change in downward acceleration.

If a fall occurs by a user inside an elevator being accelerated upward, there may be no significant change in acceleration and verification of completion of a fall is performed using distance measurements to ground or floor.

Bus travel especially while standing may appear as free falling due to abrupt changes in acceleration and/or orientation and exercise may appear as falling in situations such as squats due to sudden distance changes to the floor and abrupt acceleration changes.

Thus, there is a need and it would be advantageous to have a real time fall detection and fall related injury prevention device wearable on the waist of a user, which is capable of minimizing false positive activations of the protection elements of the device.

Referring now to the drawings, reference is now made to FIG. 1 which illustrates a protection belt 12 worn by a person, according to feature of the present invention. Protection belt 12 is shown worn around the waist of the person. On protection belt 12 on the left and right sides of the person are shown two distance sensors 10L and 10R respectively.

Protection belt includes one or more acceleration sensors or accelerometers and orientation sensors, e.g. gyroscopes (both are internal to protection belt 12 and not shown in FIG. 1)

It is useful to attach a coordinate system Ox,y,z to protection belt 12. Protection belt 12 lies in the xy plane. The z axis determines the orientation of the xy plane. Orientation kinematics may be used to determine relative orientation of protection belt 12 relative to global coordinate system OXYZ. Both the global co-ordinate system XYZ and protection belt 12 coordinate system Oxyz share an origin O. Shown in FIG. 1 are the three Cartesian axes x,y,z coordinate system Ox,y,z about which rotational angles pitch, roll and yaw are defined. The z axis corresponds to the longitudinal axis (feet to head) of the person. The y axis is a horizontal axis intersecting the person from right to left. The x axis is a horizontal axis intersecting the person from back to front.

Falling forward corresponds to a positive pitch angle $\theta_{pitch}$ around the y axis as shown. Falling to the right side corresponds to a positive roll angle $\theta_{roll}$. Falling to the left side corresponds to a negative roll angle $\theta_{roll}$. The person turning about vertical z axis to his right while standing corresponds to a positive yaw angle $\theta_{yaw}$. The person turning about vertical z axis to his left corresponds to a negative yaw angle $\theta_{yaw}$.

Figure 2:
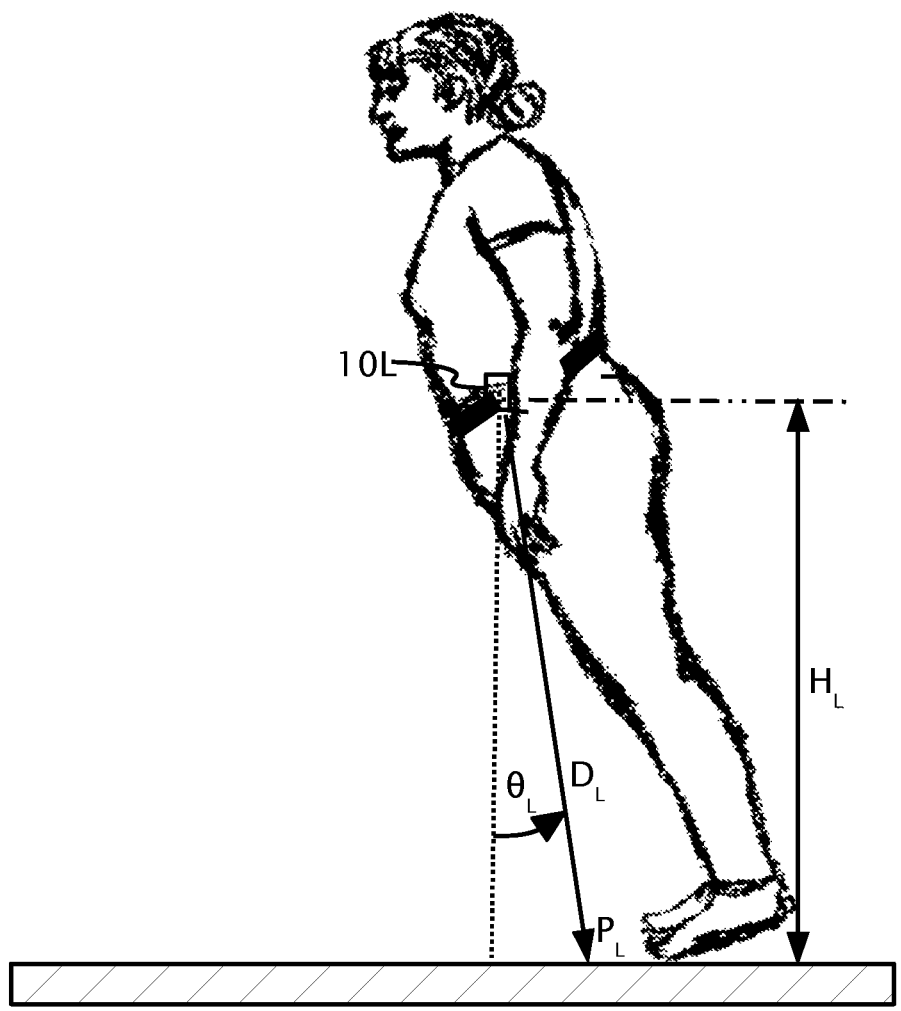
FIG. 2 illustrates a side view of person wearing an embodiment of a detection device worn by the person, according to feature of the present invention.

Reference is now made to FIG. 2 which illustrates a side view of person wearing a protection belt 12 worn by the person, according to a feature of the present invention. Left side distance sensor 10L is shown. The point-to-point distance D is shown between distance sensor 10L and the ground point $P_L$ in the direction of the propagation of the light beam emanating from distance sensor 10L. The orientation angle $\theta_L$ is shown between a ray from distance sensor 10L to ground point $P_L$ and the normal to the ground surface or floor from distance sensor 10L. The height $H_L$ from the ground surface or floor is shown between distance sensor 10L and the ground surface. In general, the mathematical relationship between distance D and height H is:

$$\cos\theta(\theta_{roll}, \theta_{pitch}, \theta_{yaw}) = \frac{H}{D} \qquad (1)$$

where the orientation angle θ may be derived from angles $\theta_{pitch}$, $\theta_{roll}$, $\theta_{yaw}$ by geometrical rotation operations or a direction cosine matrix.

Figure 3A:
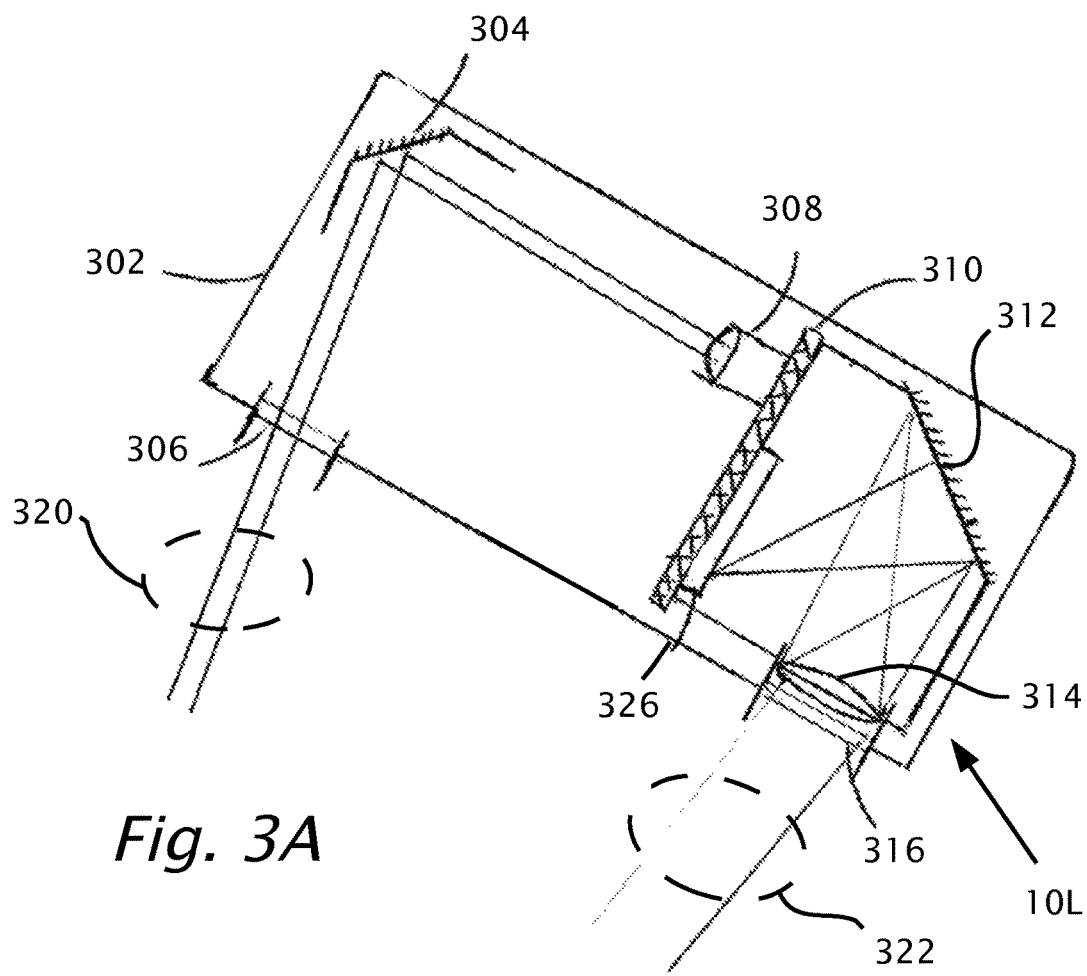
FIG. 3A illustrates an internal side view of an exemplary distance sensor, according features of the present invention.
Figure 3B:
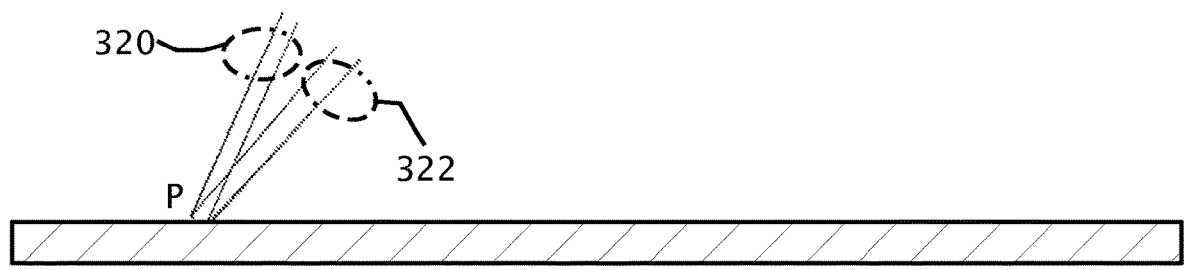
FIG. 3B, illustrates the transmitted beam from the distance sensor of FIG. 3A and the scattered beam scattered or reflected from the ground surface.

Reference is now made to FIG. 3A which illustrates a side view of an exemplary distance sensor 10L with lid removed showing further internal details of distance sensor 10L, according features of the present invention. Light source, e.g. laser diode 308 is shown mounted on a printed circuit board (PCB) 310 which is shown as edge mounted on a housing 302 of distance sensor 10L. Laser diode 308 is shown emitting a beam bounded by two incident rays which are reflected from a mirror 304 and through a window 306 as transmitted beam 320. Referring now also to FIG. 3B, transmitted beam 320 from distance sensor 10L is shown scattered from the ground surface. A portion of the scattered light is shown as beam 322 which enters into distance sensor 10L via window 316 and through optical lens 314. Rays emanating from optical lens 314 are reflected off detector mirror 312 onto the surface of a linear optical detector 326. Window 316 and optical lens 314 are both mounted in housing 302 and optical detector 316 is mounted on PCB 310. The linear position on linear optical detector 326 of the light detected from beam 322 on the surface of optical detector 326 is responsive to the distance $D_L$ shown in FIG. 2 between sensor 10L and the point $P_L$ on the ground. Distance sensors 10L and 10R may be the laser distance sensors ILR1030/1031 by Micro-Epsilon™ (MICRO-EPSILON Headquarters Koenigbacher Str. 15.94496 Ortenburg/ Germany).

Figure 4:
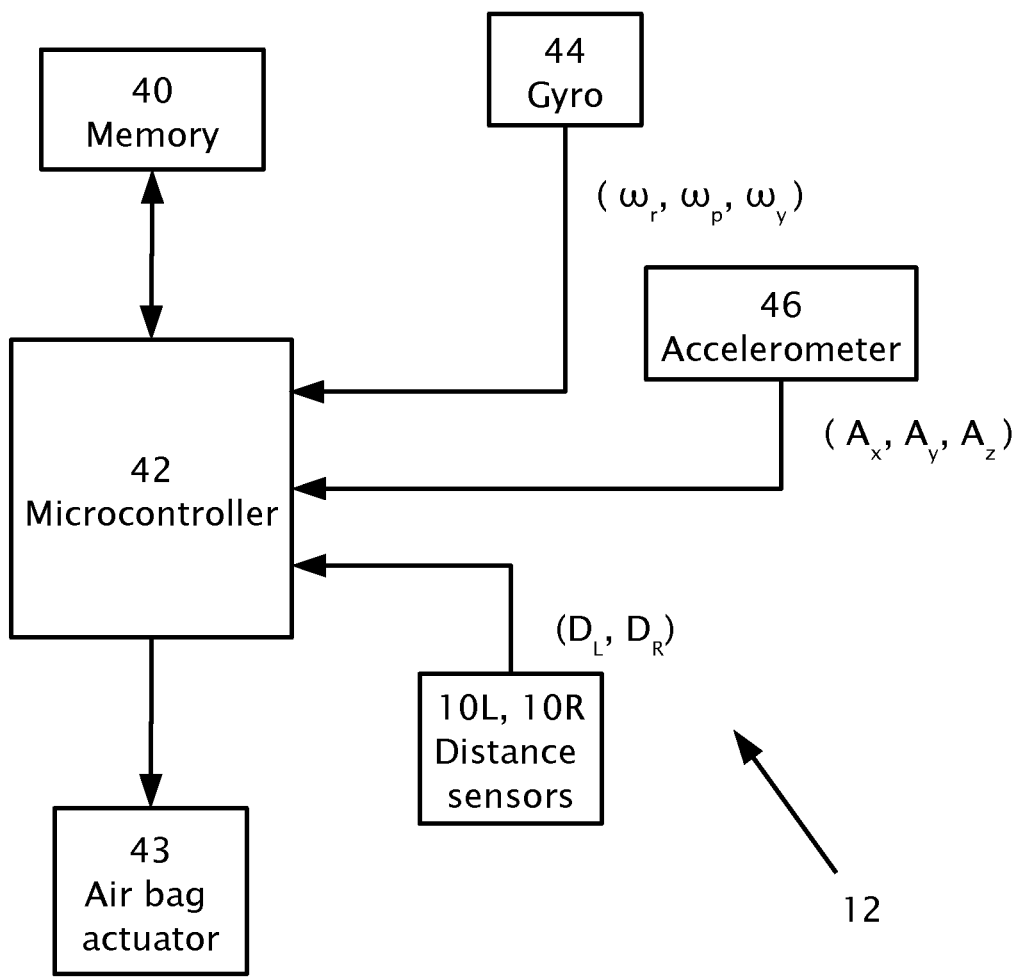
FIG. 4 illustrates a system block diagram of a fall detection device, according to features of the present invention.

Reference is now made to FIG. 4 which shows a system block diagram of hip protection belt 12, according to features of the present invention. A micro-controller or processor 42 is connected bi-directionally to memory 40. Inputs to micro-controller 42 include an output of gyroscopic sensor 44 which provides analogue or digital signals proportional to angular velocities $\omega_r$, $\omega_p$, and $\omega_y$ of roll, pitch and yaw respectively in units of radians per second for instance. An example of gyroscopic sensor 44 is MEMS motion sensor: three-axis digital output gyroscope (part no. L3GD20, STMicroelectronics™ HUNTSVILLE, Ala., 303 Williams avenue, Suite 1011, 35801, USA). Further inputs to micro-controller 42 include the output of accelerometer 46 which provides a data measure of accelerations $A_x$, $A_y$, and $A_z$ along Cartesian axes xyz respectively in units of meters per square second for instance). An example of accelerometer 46 is the accelerometer (part no. ADXL325BCPZ-RL7) by Analog Devices (One Technology Way, P.O. Box 9106, Norwood, Mass. 02062-9106, U.S.A). Yet further inputs to micro-controller 42 include the output of distance sensor/s 10L and 10R which provides a measure of distance between distance sensor 10L and the ground point $P_L$ and distance between distance sensor 10R and the ground point $P_R$ as distances $D_L$ and $D_R$ respectively (in meters for instance). Micro-controller 42 provides an output to air bag actuator 43 which is responsive to the real time inputs from distance sensors 10L and 10R, accelerometer 46 and gyroscopic sensor 44. Accelerometer 46 and/or gyroscopic sensor 44 may be co-located with a particular distance sensor 10, and/or may be located in other part(s) of protection belt 12 and/or wearable on another part of the body of the user. Wireless communication may also be utilized to supply measurement data from various distance sensor/s 10, accelerometers 46 and gyroscopic sensors 44 located at various points of the body and/ or protection belt 12 to micro-controller 42.

Figure 5:
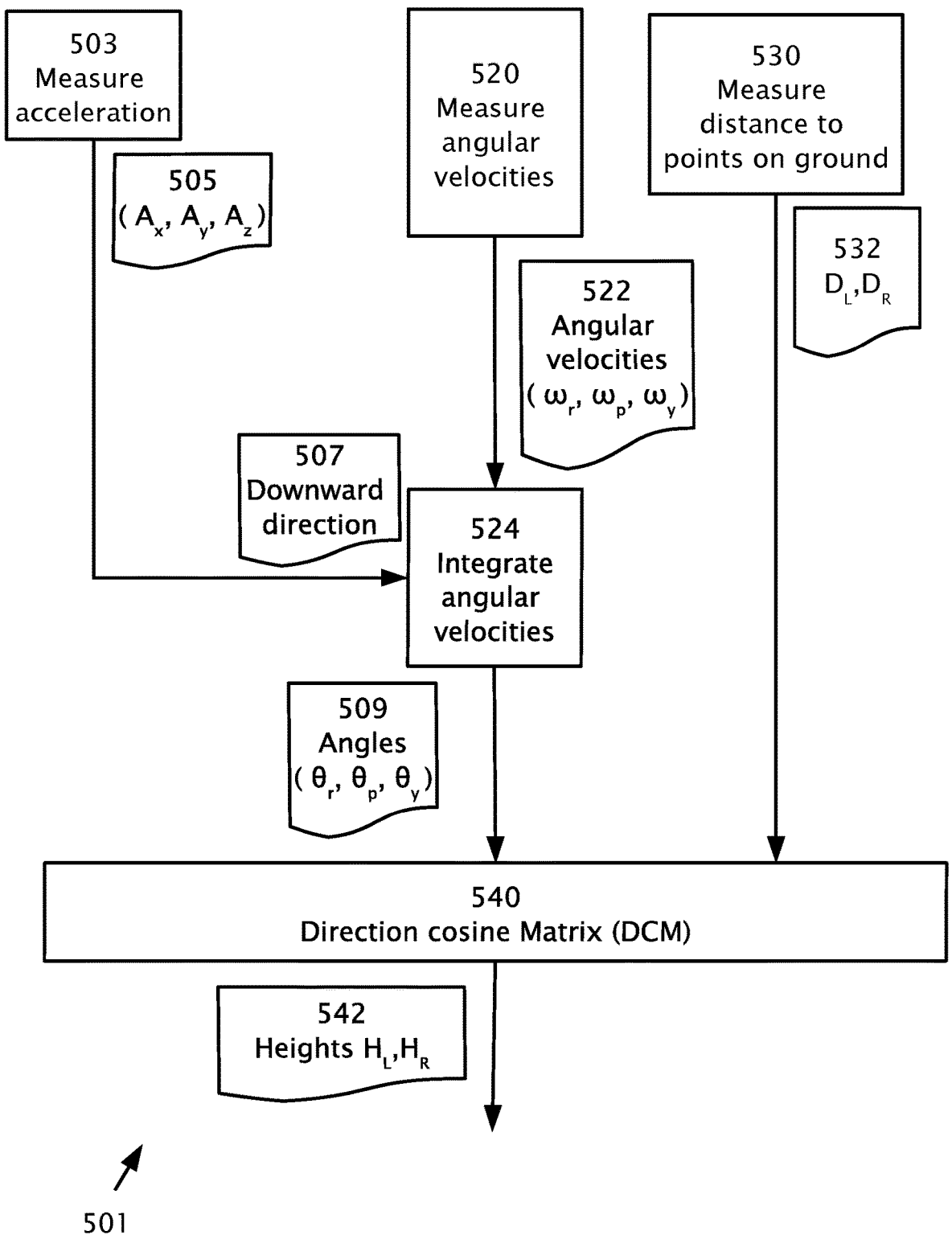
FIG. 5 illustrates a flow chart of a method of operation of a fall detection device, according to features of the present invention.

Reference is now also made to FIG. 5 which shows a flow chart of a method 501 for use of protection belt 12, according to features of the present invention. Method 501 is implemented as an algorithm run on micro-controller 42. Steps 503, 520, 524 and 530 may be performed simultaneously. With a user wearing belt 12, accelerations 505 $A_x$, $A_y$, and $A_z$ are measured in step 503. The downward direction 507 is determinable from measured accelerations 505 $A_x$, $A_y$, and $A_z$. When the user is not moving and standing for a period of time, accelerometer 46 outputs essentially the constant acceleration of gravity in downward direction 507. Alternatively, when the user is moving, the downward direction of gravity may be approximated by processing the measured accelerations 505 such as by averaging accelerations 505 over time which may approximate to downward direction 507 of gravity.

Angular velocities $\omega_r$, $\omega_p$, and $\omega_y$ are measured in step 520. Angular velocities 522 $\omega_r$, $\omega_p$, and $\omega_y$ are integrated in step 524 relative to the downward direction of gravity to provide roll, pitch and yaw rotational angles ($\theta_r$, $\theta_p$, and $\theta_y$) 509 which are produced for roll, pitch and yaw respectively relative to the downward direction of gravity.

In step 530 distances 532 $D_L$, $D_R$ are measured for each distance sensor 10L and 10R respectively.

Measured distances 532 $D_L$, $D_R$, and roll, pitch and yaw rotational angles ($\theta_r$, $\theta_p$, and $\theta_y$) 509, are input to direction cosine matrix 540 formalism to determine orientational angles $\theta_L$, $\theta_R$ between the respective light rays from distance sensor 10L, 10R respectively to ground points $P_L$, $P_R$ and the normal to the ground surface or floor.

Heights $H_L$, $H_R$ 542 are calculated from orientation angles $\theta_L$, $\theta_R$.

Figure 6:
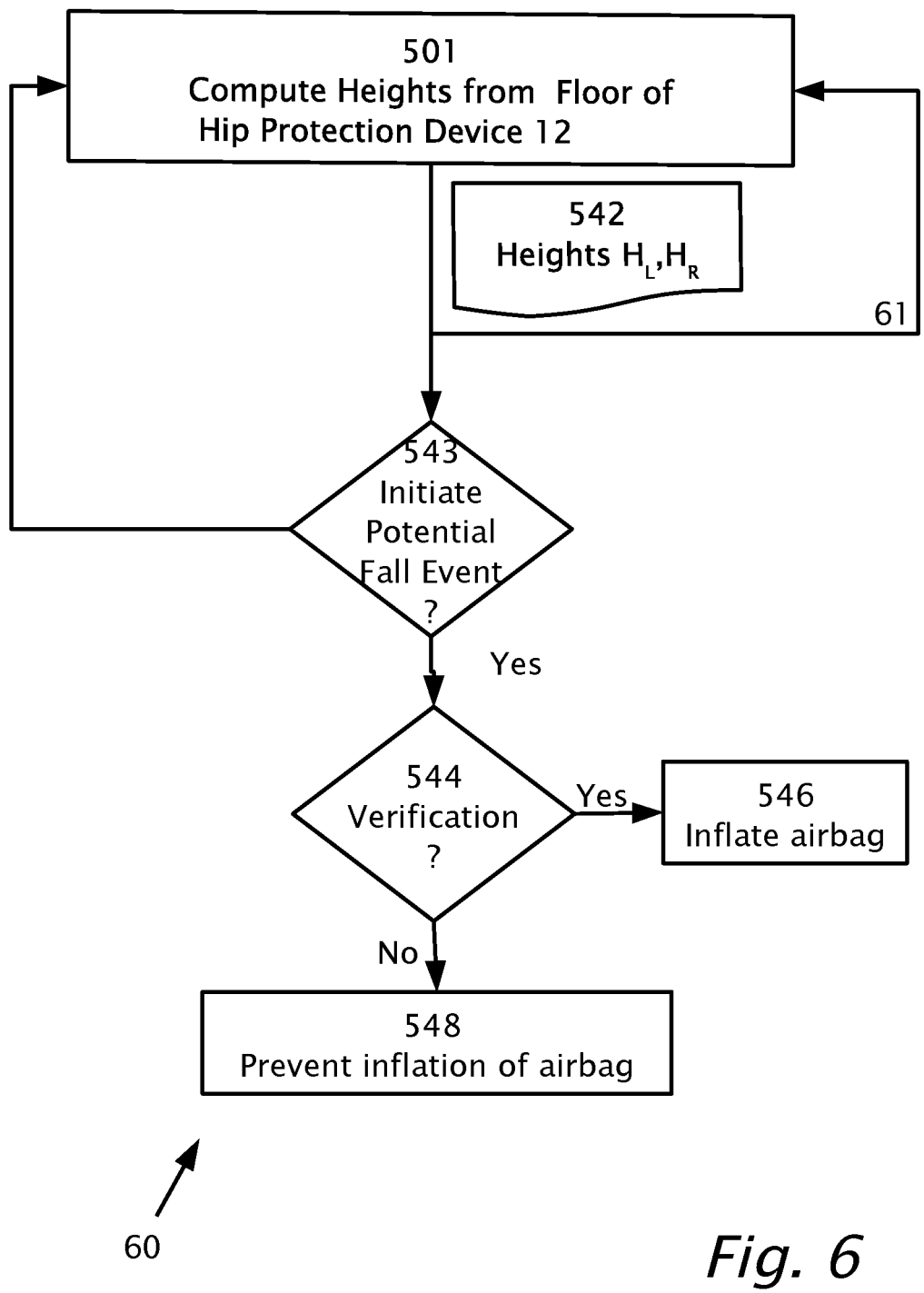
FIG. 6 is a flow diagram illustrating further features of the present invention.

Reference is also now made to FIG. 6 which is a flow diagram 60 illustrating features of the present invention. The initial height is for example standing waist height of a user which is approximately one meter. One or more heights $H_L$, $H_R$ from protection belt 12 to the ground surface or floor is computed in a repeated fashion as shown by feedback loop 61. The repetition rate in measurements per second or sampling rates of the height computation 501 may be under control of micro-controller 42. A rapid decrease in in heights $H_L$, $H_R$ may be taken as in indication of a potential fall in decision block 543. However, a number of false positive indications are preferably eliminated by verification (step 544) of completion of a fall before optionally activating or inflating (step 546) airbag of detection device 12. To reliably detect true falls, one or more redundant height computations (step 501) may be performed after initiation of a potential fall event 543. More height computations may be used to increase reliability in detecting a real fall. Height computations $H_L$, $H_R$ may be provided throughout the fall as a means to avoid false positive fall detections.

Prevention of inflation (step 548) of an air-bag may occur in potential fall situations when exercising and the decrease in measured heights is controlled and repetitive. Abruptly sitting in a chair is eliminated as a positive indication of a fall and the airbag is prevented from inflating (step 548) when the height measured is not continuous, the distance sensor generally measures a distance to the floor followed by a much shorter distance to the chair.

Use of Inertial Sensors

Inertial sensors, gyroscope 44 and/or accelerometer 46 may be used to determine a change in velocity $\Delta V_Z$ and change in height $\Delta Z$ as follows:

$$\Delta V_Z = (g - a_Z) \times \Delta t \quad (2)$$

$$\Delta Z = Z_2 - Z_1 \quad (3)$$

where g is the downward acceleration of gravity, $a_z$ is the downward acceleration derived from the accelerometer. The downward direction may be determined at least in part from gyroscope 44 orientation information. $\Delta t$ is the time interval between measurements. Indices 1,2,3 . . . indicate measurements over time t.

Based on the inertial sensors, gyroscope 44 and/or accelerometer 46 a new vertical distance value $Z_2$ value may be predicted as follows using kinematics:

$$Z_2 = \frac{(g - a_Z) \times \Delta t^2}{2} + Z_1 \quad (4)$$

Even after one (or more) of the distance sensors 10 is temporarily blocked, a single distance measurement after a fall event (and preferably during the final 200 milliseconds of a fall) may be sufficient to verify and predict completion of a fall event by correlating the measurements using distance sensors 10 with predictions from the inertial sensors.

Referring back to FIG. 6, verification (step 544) may be performed as follows according to an embodiment of the present invention.

Initiation of a potential fall event is measured or computed, (a significant decrease in downward acceleration or height).

A downward acceleration based on inertial sensors may determine a threshold height (e.g. 40 centimeters) and a time $t_f$ at which completion of a fall is expected to be imminent. The threshold height may be previously determined or previously calibrated based on user performance. The threshold height may vary between 30 and 50 centimeters.

A predetermined time interval, e.g. 100-300 milliseconds is chosen prior to a time $t_f$ at which completion of a fall is expected to be imminent. During the predetermined time interval one or more heights 542 are computed (step 501) from previously stored results. The computed heights 542 $H_L$, $H_R$ during the predetermined time interval prior to time $t_f$ are used to verify the completion of the fall and optionally (step 546) a protective device such as an air bag may be activated after verification.

Various validation/correlation options are available:

Height calculated from accelerometers and gyroscopes can be validated with height measured by distance sensors.

Velocity towards ground may be calculated from heights $H_L$, $H_R$ 542 (FIG. 5) and compared with velocity towards ground $V_z$ estimated from inertial sensors.

Continuity of velocity towards ground $V_z$ may be compared to actual fall scenarios.

Downward acceleration may be determined to be consistent with a real fall either/both from double differentiation of computed heights $H_L$, $H_R$ 542 and/or from differentiation of change in downward velocity $\Delta V_Z$ as determined from the inertial sensors.

The pattern of vertical height change $\Delta Z$ may be used and compared with those of actual fall scenarios.

The term "simultaneously" as used herein in the context of simultaneous measurements refers to time differential between measurements of different sensors on the order of or less than one millisecond. The terms "real time" and/or monitor or sample "over time" as used herein refers to a maximum time latency between the time of an event, e.g. a measurement and the processing of an event as less than 100 milliseconds.

The term "user" as used herein may be a person, an animal or a machine such as an android robot.

The term "downward" as used herein refers to the direction of the pull of gravity.

The "upward" direction is positive and the "downward" direction is negative.

The term "sampling rate" as used herein refers to a rate of measurement by a sensor in units of number of measurements per unit time (such as 200 measurements per second) of for example distance, acceleration and/or angular velocity.

The term "discontinuous" as used herein in the context of "discontinuous" height measurements" refers to a change in computed height greater than 20% of waist height in standing position (typically 100 cm).

The term "change" as used herein in the context of change of downward acceleration measurements" refers to a decrease in downward acceleration greater than 20% (or a measured downward acceleration change from the acceleration of gravity g to 0.8 g at least).

The term "rapid" in the context of "rapid" decrease in heights refers to a decrease greater than 20% of the current or default height measurement over time period of 200 milliseconds or less.

The term "initiation of potential fall event" as used herein refers to a measurement of "rapid" decrease in computed heights or a measurement of a change in acceleration in the downward direction.

The terms as used herein "before" initiation of a potential fall event and "after" the initiation of the potential fall event in the context of height computations or determinations refers to the at least two computations from sampled measurements separated in time by at least 200 milliseconds.

The articles "a", "an" is used herein, such as "an air bag", "a sensor", "a data parameter" have the meaning of "one or more" that is "one or more air bags", "one or more sensors" and "one or more data parameters".

The present application is gender neutral and personal pronouns 'he' and 'she' are used herein interchangeably.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

Although selected features of the present invention have been shown and described, it is to be understood the present invention is not limited to the described features. Instead, it is to be appreciated that changes may be made to these features without departing from the principles of the invention, the scope of which is defined by the claims.

The invention claimed is:

1. A device wearable by a user, the device comprising:
a processor;
an acceleration sensor operatively attached to the processor, wherein the acceleration sensor is configured to sense an acceleration vector of the device;
a gyroscope sensor operatively attached to the processor, wherein the gyroscope sensor is configured to sense an angular velocity of the device;
a distance sensor operatively attached to the processor, wherein said distance sensor is oriented to measure a point-to-point distance between the device and a point on a ground surface;
wherein the processor is configured to time sample and to input a plurality of respective values over time of: the acceleration vector, the angular velocity and the point-to-point distance;
wherein the processor is configured to determine over time the direction of gravity from the acceleration vector;
wherein the processor is configured to integrate over time the angular velocity to produce an orientation angle of the device relative to the direction of gravity;
wherein the processor, responsive to the point-to-point distance and the orientational angle, is configured to compute heights over time of the distance sensor from the ground surface;
wherein the processor is configured to indicate initiation of a potential fall event by a change in downward acceleration measured by the accelerometer or a rapid decrease in the determined heights of the distance sensor from the ground surface;
wherein the processor is configured, responsive to the point-to-point distance and the orientation angle, to compute a height of the distance sensor from the ground surface before the initiation of the potential fall event and a height of the distance sensor from the ground surface after the initiation of the potential fall event,
wherein the processor, when a computed height is less than a predetermined threshold height, is configured to determine completion of a fall at a time $t_f$ and to compute said height of the distance sensor after the initiation of the potential fall event based on stored results from a measurement recorded at a time during a previously determined time interval prior to the time $t_f$.

2. The device of claim 1, wherein the previously determined time interval is selected between 100 and 300 milliseconds prior to the time $t_f$.

3. The device of claim 1, wherein the processor is configured to verify an expectation of completion of a fall by correlating said height after the initiation of a potential fall event with a computed height predicted from a simultaneous measured acceleration component in the downward direction.

4. The device of claim 1, wherein the processor is configured to verify an expectation of completion of a fall by correlating a velocity determined from said height before the initiation of the potential fall event and said at least one height after the initiation of the potential fall event with a velocity predicted by integrating a simultaneous measured acceleration component in the downward direction.

5. The device of claim 1, wherein the processor is configured to verify an expectation of completion of a fall by correlating a downward acceleration determined from said height before the initiation of the potential fall event and said height after the initiation of the potential fall event with a simultaneous measured acceleration component in the downward direction.

6. The device of claim 1, further comprising:
an airbag operatively connectable to the processor, wherein the air bag, responsive to an activation by the processor, is configured to protect the user from a fall.

7. The device of claim 6, wherein the processor is configured to activate the airbag when the computed heights rapidly decrease over time except: (i) when the decrease of the computed heights is followed by an increase in computed heights indicating that the user is exercising or (ii) when said height before the initiation of the potential fall event and said height after the initiation of the potential fall event are substantially uncorrelated with a computed height predicted from simultaneous measured acceleration in the downward direction as measured by the accelerometer characteristic of the user standing on a means of transportation or (iii) when the heights computed are discontinuous over time indicating that the variations in heights are characteristic of being computed from a ground surface to being computed from an object on the ground surface or (iv) when the decrease of height computations is characteristic of the user ascending or descending a stairway.

8. A method for fall detection, using a device wearable by a user, wherein the device includes: a processor and operatively attached to the processor, an acceleration sensor, a gyroscope sensor, and a distance sensor, the method comprising:
sampling over time and thereby inputting a plurality of respective values over time of an acceleration vector and an angular velocity, and measuring a point-to-point distance between the distance sensor and a point on a ground surface;
determining the direction of gravity from the acceleration vector;
integrating the angular velocity to produce an orientation angle of the device relative to the direction of gravity;
indicating initiation of a potential fall event by a change in downward acceleration measured by the accelerometer or a rapid decrease in the computed heights of the distance sensor from the ground surface;
responsive to the point-to-point distance and the orientation angle, computing a height of the distance sensor from the ground surface before the initiation of the potential fall event and a height after the initiation of the potential fall event of the distance sensor from the ground surface; and
upon a computed height less than a predetermined threshold height, determining completion of a fall at a time $t_f$ and computing said height of the distance sensor after the initiation of the potential fall event based on stored results from a measurement recorded at a time during a previously determined time interval prior to the time $t_f$.

9. The method of claim 8, wherein the previously determined time interval is selected between 100 and 300 milliseconds prior to the time $t_f$.

10. The method of claim 8, further comprising:
verifying an expectation of completion of a fall by correlating said height after the initiation of the potential fall event with a computed height predicted from a simultaneous measured acceleration component in the downward direction.

11. The method of claim 8, further comprising
activating an airbag when the computed heights rapidly decrease except: (i) when the decrease of the computed heights is followed by an increase in computed heights indicating that the user is exercising or (ii) when said height before the initiation of the potential fall event and said e height after the initiation of the potential fall event are substantially uncorrelated with a computed height predicted from simultaneous measured acceleration in the downward direction as measured by the accelerometer characteristic of the user standing on a moving means of transportation, or (iii) when the heights computed are discontinuous over time indicating that the variations in height are characteristic of being computed from a ground surface to being computed from an object on the ground surface or (iv) when the decrease of height computations is characteristic of the user ascending or descending a stairway.

12. The method of claim 8, wherein the acceleration vector as sensed by the acceleration sensor includes a constant acceleration of gravity and dynamic acceleration due to movement of the user, wherein the direction of gravity is determined by at least one algorithm selected from the group consisting of:
(i) determining that the user wearing the device is not moving and the direction is determined by the constant acceleration of gravity; and
(ii) averaging the acceleration vectors over a time period while the user wearing the device is moving and determining the direction of gravity from the resultant average.

13. The method of claim 11, further comprising:
preventing activation of the airbag when the acceleration sensor indicates a rapid change in acceleration characteristic of elevator usage unaccompanied by a rapid decrease in the heights of the distance sensor from the ground surface.

14. The method of claim 8, further comprising:
verifying the potential fall event as a real fall event if the height after the initiation of the potential fall event is substantially correlated with a computed height predicted from simultaneous measured acceleration in the downward direction as measured by the accelerometer.

15. The method of claim 8, further comprising:
upon said indicating the initiation of the potential fall event, increasing measurement sampling rate for computation of height and computing said height after the potential fall event at a higher sampling rate.

16. The method of claim 11, further comprising:
preventing activation of the airbag when said height after the initiation of the potential fall event does not continue to decrease.

17. The method of claim 11, further comprising:
preventing activation of the airbag when the said at least one height after the initiation of the potential fall event does not continue to decrease and indicates that the user is standing on a moving means of transportation.

18. The method of claim 11, further comprising:
preventing activation of the airbag when said height after the initiation of the potential fall event does not continue to decrease thereby indicating that the height computations vary from being measured from a ground surface to being measured from an object placed on the ground surface.

19. The method of claim 11, further comprising:
preventing activation of the airbag when the decrease of height computation is characteristic of the user ascending or descending a stairway.

20. The method of claim 11, further comprising:
preventing activation of the airbag when the acceleration sensor indicates a discontinuous change in acceleration characteristic of elevator usage unaccompanied by a rapid decrease in the computed heights of the distance sensor above the elevator floor.

* * * * *